United States Patent [19]

Fannin et al.

[11] 4,127,507

[45] Nov. 28, 1978

[54] HYDROCARBON SOLUBLE STRAIGHT-CHAIN DI-(LOWER ALKYL) MAGNESIUM COMPOSITIONS

[75] Inventors: Loyd W. Fannin, Dickinson; Dennis B. Malpass, LaPorte, both of Tex.

[73] Assignee: Texas Alkyls, Inc., Deer Park, Tex.

[21] Appl. No.: 811,339

[22] Filed: Jun. 29, 1977

[51] Int. Cl.$^2$ .......................... B01J 31/12; C08F 4/50
[52] U.S. Cl. ............................ 252/431 R; 260/665 R; 260/665 G
[58] Field of Search ............... 252/431 R; 260/665 G, 260/665 R

[56] References Cited

U.S. PATENT DOCUMENTS

| | | | |
|---|---|---|---|
| 3,264,360 | 8/1966 | Nudenberg et al. | 260/665 G |
| 3,646,231 | 2/1972 | Kamienski et al. | 260/665 R |
| 3,737,393 | 6/1973 | de Vries | 252/431 R |
| 3,903,019 | 9/1975 | Hargis et al. | 252/431 R |

OTHER PUBLICATIONS

Emeleus et al., *Advances in Inorganic Chemistry & Radioindustry*, vol. 11 (1968), pp. 343-345, Academic Press, N.Y., N.Y.

*Primary Examiner*—Patrick P. Garvin
*Attorney, Agent, or Firm*—M. Henry Heines

[57] ABSTRACT

A composition of matter comprising di-n-butylmagnesium and diethylmagnesium with a n-butyl:ethyl alkyl group ratio of about 0.25:1 to about 4:1 which is soluble in aliphatic, cycloaliphatic, and aromatic hydrocarbon solvents is disclosed. The composition is prepared in the substantial absence of oxygen and moisture by the simultaneous or consecutive reactions of ethyl and n-butyl halides with metallic magnesium in the presence of the hydrocarbon solvent, followed by separation of the insoluble magnesium chloride and any unreacted magnesium metal from the resulting solution.

19 Claims, No Drawings

HYDROCARBON SOLUBLE STRAIGHT-CHAIN DI-(LOWER ALKYL) MAGNESIUM COMPOSITIONS

BACKGROUND OF THE INVENTION

Diorganomagnesium compounds are well known for their usefulness in a wide variety of chemical reactions. As reagents, these compounds can be used for the reduction of ketones, the metalation of aromatic compounds, are the alkylation of metal halides or oxides to the corresponding metal alkyls. As catalysts, diorganomagnesium compounds are useful in the dimerization and polymerization of olefins, see U.K. Pat. No. 1,251,177, the polymerization of epoxides, see U.S. Pat. No. 3,444,102, and the preparation of telomers, see U.S. Pat. No. 3,742,077. While they perform many of the same types of functions performed by Grignard reagents, diorganomagnesium compounds, owing to differences in electronic and steric factors, are more reactive than Grignard reagents toward certain types of compounds. In general, see also U.S. Pat. Nos. 3,646,231 and 3,822,219.

The utility of diorganomagnesium compounds is lessened by the fact that they are highly viscous liquids or solids which are unstable upon exposure to moisture and air. This problem is generally overcome either by dissolving the compound in an inert hydrocarbon solvent or by solvating the compound. Many diorganomagnesium compounds, particularly those with straight chain lower alkyl groups, are insoluble by themselves in hydrocarbon solvents and thus require solubilizing agents which will form a soluble complex. Examples of such solubilizing agents are alkyllithium compounds, see U.S. Pat. No. 3,742,077, dialkyl zinc compounds, see U.S. Pat. No. 3,444,102, alkali metal hydrides, see U.S. Pat. No. 3,655,790, and organoaluminum compounds, see U.S. Pat. Nos. 3,737,393 and 3,028,319.

Solvation involves the use of an ether or an organic base molecule to associate directly with the magnesium atom, thus rendering a liquid-phase complex. The solvated form is undesirable, however, since solvation seriously inhibits the effectiveness of the compound, particularly when the compound is used as a Ziegler-type catalyst. The use of ether is particularly undesirable due to considerations of flammability and explosibility.

Solubilization also serves to reduce the viscosity of reaction mixtures whose high viscosity would otherwise inhibit the progress of the reaction and cause difficulty in handling and transferring. This problem is only partially solved by the use of chloroaryl solvents to form low viscosity suspensions of the insoluble compounds, as described in U.S. Pat. No. 3,264,360.

In addition, the insolubility of the lower alkyl magnesium compounds makes preparation of them in a form free of undesirable halides difficult. In particular, the direct reaction of magnesium metal with an organic halide is disclosed in Glaze and Selman, *Journal of Organometallic Chemistry*, Vol. 5, p. 477 (1967), and W. N. Smith, *Journal of Organometallic Chemistry*, Vol. 64, p. 25 (1974). These articles deal with the preparation of diorganomagnesium compounds with straight chain alkyl groups of 5 carbon atoms and higher. Such compounds are soluble in hydrocarbon solvents and thus readily separable from the concurrently produced magnesium halide and unreacted magnesium. When lower straight chain alkyls are used in this process, the desired diorganomagnesium compound is formed but is insoluble and exists as a slurry in the solvent together with the magnesium halide and unreacted magnesium metal. Thus a solubilizing agent is required when this process is used to make lower alkyl diorganomagnesium compounds. The latter are particularly desirable as reagents and catalysts owing to their relatively high magnesium content on a weight basis.

Other methods of preparation include the mercurymagnesium exchange method, as disclosed in Cowan and Mosher, *Journal of Organic Chemistry*, Vol. 27, p. 1 (1962), and the dioxanate-precipitation method, as disclosed in Schlenk, *Berichte der Deutschen Chemischen Gesellschaft*, Vol. 64, p. 734 (1931). The mercury method,

$$R_2Hg + Mg \rightarrow R_2Mg + Hg$$

where R is alkyl, is limited by the high cost of dialkylmercury compounds, and the health hazards involved in their use. The reaction itself is hazardous since it proceeds rapidly and exothermically after an inhibition period.

The dioxanate-precipitation method,

$$2RMgX + C_4H_8O_2 \xrightarrow{ether} R_2Mg + C_4H_8O_2 \cdot MgX_2 \downarrow$$

where R is alkyl and X is halogen, involves removal of magnesium halide from either solutions of Grignard reagents by precipitation of a complex which the dioxane forms with the halide. This is a tedious process and results in an etherated dialkylmagnesium complex from which the ether must be removed prior to use as a catalyst.

Dialkylmagnesiums can also be prepared from alkyllithiums, see U.S. Pat. No. 3,646,231, by precipitation of lithium halide,

$$MgX_2 + 2RLi \rightarrow R_2Mg + 2LiX$$

where R is alkyl and X is halogen. This process is unsuitable for straight-chain lower alkyl diorganomagnesiums which are insoluble in hydrocarbon solvents, since separation will be impossible. The use of basic solvents renders separation possible but requires subsequent desolvation. This reference also discloses the use of a hydrocarbon-soluble diorganomagnesium to solubilize an insoluble diorganomagnesium. The solubilizing members shown in this reference, however, invariably contain branched chain alkyl groups. Such branched chain diorganomagnesium compounds cannot be prepared by the Glaze and Selman method mentioned above. This fact is established in the work of Kamienski and Eastham, *Journal of Organic Chemistry*, Vol. 34, p. 1116 (1968). Thus, resort to the lithium halide precipitation method is required. The use of two individually insoluble straight chain diorganomagnesium compounds to mutually solubilize each other has not been disclosed, particularly two such compounds which can be prepared by the direct reaction between magnesium metal and alkyl halide.

British Pat. No. 1,251,177 discloses ethylbutylmagnesium as well as other dialkylmagnesiums for use as polymerization co-catalysts. The dialkylmagnesiums are disclosed as soluble at extremely low concentrations only. In particular, di-n-butylmagnesium, the only nonaromatic magnesium compound shown in the actual working examples, is not soluble at concentrations in excess of about 0.1% by weight in terms of its magnesium content. Thus, there is no inference from the disclosure that a particular combination of straight chain lower alkyl groups will produce a soluble composition of matter at appreciable concentrations.

It is therefore an object of the present invention to provide hydrocarbon-soluble diorganomagnesium compositions of high magnesium content.

A further object of the present invention is to provide a process by which hydrocarbon soluble diorganomagnesium compositions of high magnesium content can be prepared by the direct reaction of alkyl halides with magnesium.

A still further object of the present invention is to provide a means for solubilizing straight chain lower alkyl diorganomagnesium compounds in hydrocarbon solvents.

Another object of the present invention is to provide a composition of matter comprising di-n-butylmagnesium, diethylmagnesium, and a hydrocarbon solvent.

Yet another object of the present invention is to provide a process for the manufacture of halide-free, metallic magnesium-free, and unsolvated straight-chain, lower alkyl diorganomagnesium compounds using raw materials which are less expensive than those required for existing processes.

BRIEF DESCRIPTION OF THE INVENTION

The present invention relates to the discovery that a composition of matter comprising di-n-butyl magnesium and diethyl magnesium is soluble in hydrocarbon solvents. While neither of these two compounds is soluble alone, each has the effect of rendering the other soluble. Related to this discovery is the further discovery that a hydrocarbon-soluble mixture of these two compounds can be prepared by the direct reaction of metallic magnesium with the corresponding alkyl halides in consecutive reactions. When separately prepared by this method, without being subsequently combined, the compounds are insoluble and thus inseparable from the magnesium halide formed concurrently and in equimolar amounts and from unreacted magnesium metal. The present invention thus provides a novel method for the preparation of straight-chain lower alkyl diorganomagnesium compounds in hydrocarbon solution substantially free of halides and metallic magnesium without the use of solubilizing agents or solvation.

DETAILED DESCRIPTION OF THE INVENTION

According to the present invention, di-n-butyl magnesium and diethylmagnesium are combined to provide a composition which is soluble in hydrocarbon solvents. It has been postulated that the insolubility of the individual compounds is due to intermolecular association between the compounds to form polymer-type structures wherein each magnesium atom is tetrahedrally surrounded by four alkyl groups. Known methods of solubilizing these compounds presumably operate to break down the structures into smaller units by breaking some of the alkyl-magnesium bonds. It is postulated that this occurs through an alkyl interchange and re-association effect brought about by solvation, complexing, or simple alkyl exchange with alkyl groups of longer chain lengths or branched chain configurations. Polymerization is thus sterically inhibited due to the presence of unwieldy groups, or groups which form soluble complexes on their own and thus prevent a polymeric fit. Hence, it is surprising that two independently insoluble and presumably polymer-forming dialkylmagnesiums can solubilize each other. Stated in another manner, it is surprising and unexpected that alkyl interchange between di-n-butylmagnesium and diethylmagnesium is sufficient to break down the polymer-type bonds and render the two compounds soluble in hydrocarbon solvents. Consistent with the alkyl-interchange theory, equimolar combinations of di-n-butylmagnesium and diethylmagnesium are considered equivalent to n-butylethylmagnesium. This theory is offered merely to show the unexpected nature of the composition of the present invention, and is intended neither to define nor to limit the invention in any manner.

The term "hydrocarbon solvent" is used herein to designate aliphatic, cycloaliphatic, and aromatic hydrocarbons. Illustrative of aliphatic solvents are n-pentane, isopentane, n-hexane, n-heptane, n-octane, isooctane, pentamethylheptane, and gasoline or other petroleum fractions. Illustrative of cycloaliphatic solvents are cyclohexane, methylcyclohexane, methylcyclopentane, cycloheptane, and cyclooctane. Illustrative of aromatic solvents are benzene, toluene, xylenes, ethylbenzene, tetralin, and α-methylnaphthalene. Preferred solvents are those containing 5 to 20 carbon atoms, inclusive. More preferred are those containing 6 to 15 carbon atoms, inclusive. Particularly preferred solvents are those which have boiling points between about 69° C. and about 110° C. The actual concentration of dialkylmagnesium in the solvent is not critical and the compounds are soluble over a wide range of concentration. The solution viscosity increases with concentration, however. Thus, for practical considerations of ease of handling, the dialkylmagnesium concentration is normally from about 0.2 weight percent to about 12 weight percent in terms of magnesium, preferably from about 1 weight percent to about 5 weight percent magnesium.

The individual dialkylmagnesium compounds can be prepared separately in solid form by any method known in the art and subsequently placed in contact with a hydrocarbon solvent in the presence of each other to obtain a clear solution which is readily separable from any solids retained with the compounds. Thus, either of the two dialkylmagnesium compounds, as a solid or slurry, existing in admixture with magnesium halides, lithium halides, or other insoluble by-products of the manufacturing process or unreacted starting materials, can be contacted with a hydrocarbon solvent in the presence of the other dialkylmagnesium compound, to produce a solution containing as solutes the two dialkylmagnesium compounds substantially free of the other insolubles. Solubilization can be hastened by heating the solution to a temperature of about 50° C. or higher. The rate of solubilization increases as the temperature is raised. Once the compounds are dissolved, they will remain in solution upon any subsequent lowering of temperature.

Separation of the solution from the remaining undissolved solids can be enhanced by the use of any of the variety of viscosity reducing agents known in the art. Examples of such viscosity reducers are organoaluminum compounds such as trialkylaluminums, dialkylaluminum halides, and alkylaluminum dihalides.

Alternatively, the di-n-butyl- and diethylmagnesium compounds can be prepared directly in a common vessel by either simultaneous or subsequent reactions. Any reaction is suitable in which all components produced or remaining in the system are insoluble other than the di-n-butyl- and diethylmagnesiums. It will be most convenient to use the direct reaction between metallic magnesium and n-butyl and ethyl halides. The concurrently produced magnesium chloride precipitates out of solution and is readily removed together with any unreacted magnesium from the hydrocarbon solution of the products.

Following any of the above procedures, the solids can be removed from the reaction mixture by any conventional technique, for example, centrifuging, decanting, or filtration. The resulting solution of di-n-butyl- and diethylmagnesium can then be diluted or concentrated as desired, depending on the ultimate concentration desired for purposes of reactivity, viscosity, or economic considerations.

The mutual solubilizing effect is achieved at n-butyl:ethyl mole ratios of from about 0.25:1 to about 4:1. The preferred range of mole ratio is from about 0.5:1 to about 2:1, with the most preferred range being from about 0.8:1 to about 1.25:1. Generally, the mutual solubilizing effect is not complete and a quantity of either or both of the two compounds remains undissolved. The mutual solubilizing effect increases as the n-butyl:ethyl mole ratio approaches unity from either above or below. The solubility is at its maximum at a mole ratio of approximately 1.0.

When magnesium is reacted directly with an alkyl halide, commercial grade magnesium turnings or shavings can be used. It is preferable, however, to use a form of magnesium with a higher surface area than either of the above. This can be accomplished by milling, but it is most preferable to use the metal in a finely divided state, for instance, as a powder with a particle size equal to or less than about 150 microns.

When the magnesium-ethyl halide reaction and the magnesium-n-butyl halide reaction are done in a common vessel, it is preferable to react the ethyl halide with the magnesium first, followed by addition of the n-butyl halide. This is because ethyl halide is more stable than higher alkyl halides and will react with magnesium at a slow rate unless additional means are provided for activation of the magnesium. The term "magnesium activating agent" is used herein to denote heat or any substance which, when contacted with magnesium will cause said magnesium to react with ethyl chloride at a substantially faster rate by virtue of such contact. Typical activating agents are known in the art, examples of which are the use of $AlCl_3$, $AlCl_3$-ether complexes, N,N-dimethylaniline, molecular iodine, alkyl halides of at least 4 carbon atoms, and Grignard reagents. Thermal activation is the preferred method and is generally achieved at temperatures between about 125° C. and about 350° C., preferably from about 150° C. to about 250° C., most preferably from about 150° C. to about 200° C. Once the magnesium is activated, the ethyl halide/magnesium reaction will proceed at lower temperatures. Although the reaction will occur over a wide range, it will be most convenient to operate at a temperature between about 20° C. and about 200° C., preferably between about 40° C. and about 150° C., most preferably between about 75° C. and about 125° C. The above described thermal activation method must be run in the presence of around 10% by weight (based on the weight of magnesium metal) of one or both alkyl halide reactants.

The butyl halide reaction is also operable over a wide temperature range, but is most conveniently run at a temperature between about 20° C. and about 200° C., preferably between about 60° C. and about 100° C.

None of the above temperature ranges are critical with regard to either reaction. The minimum temperature is dictated only by what would be considered an economical reaction rate, while the maximum temperature is limited only by the possibility of alkyl halide decomposition and considerations of energy conservation.

Although it is preferable to perform the ethyl halide/magnesium reaction first, followed by the n-butyl halide/magnesium reaction, the reverse order of reactions can also be used. When the n-butyl halide reaction is performed first, care must be taken to avoid or eliminate the coating of unreacted magnesium metal with solid di-n-butylmagnesium. Such coating can severely hinder the subsequent reaction of ethyl chloride with the magnesium by preventing contact between the reactants. This problem can be avoided by the use of a large amount of solvent, extra agitation, a slow rate of addition of n-butyl chloride, or the addition of excess magnesium. The n-butyl chloride can also be used as an activator for the magnesium in the ethyl chloride reaction if a small amount of n-butyl chloride is added prior to the ethyl chloride addition, and the remainder after the ethyl chloride addition.

The term "halide" as used herein denotes chloride, bromide, or iodide, or combinations thereof. Chlorides are generally preferred for reasons of economy.

The magnesium and the alkyl halides are normally reacted in a mole ratio of the magnesium to the total halides of 1.2, i.e., a 20% overall molar excess of magnesium. It is understood, however, that the overall mole ratio can be varied in the range from about 1 to about 2 moles of magnesium per mole of halide, and preferably in the range from about 1.1 to about 1.3, i.e., about 10-30% overall excess magnesium. This excess magnesium is desirable to minimize Wurtz coupling reactions.

The hydrocarbon solvent may be added before, during, or after the reaction. It will be most convenient to add the solvent prior to or during the ethyl halide reaction, so that further reaction is less inhibited by high viscosity.

Due to the pyrophoric nature of the system components, and also to prevent the undesirable formation of magnesium oxide, the reactions must be carried out in the absence of more than trace amounts of oxygen. Thus, the reactions are normally carried out in an atmosphere of inert gas such as nitrogen or argon, or in an atmosphere of ethyl halide gas. The reactions must also be conducted in the substantial absence of water, due to the susceptibility of the system components to decomposition in the presence of water.

The pressure under which the reactions are conducted in not critical and pressures ranging from atmospheric to elevated pressures of several atmospheres can be employed. The ethyl halide reaction will be most conveniently run at pressures at least in slight excess of atmospheric in order to keep the ethyl halide in solution. The preferred pressure range is about 8 psig ($1.6 \times 10^5$ pascals) to about 100 psig ($8.0 \times 10^5$ pascals). Lower pressures can be used with the butyl halide reaction.

The present invention is further illustrated by the following examples.

EXAMPLE 1

An aerosol compatibility test bottle reactor was charged with 9.0 g (0.370 g-atom) of 100-mesh magnesium powder and placed in an oil heating bath at 160° C. The reactor was then purged with ethyl chloride gas and allowed to reach thermal equilibrium at a pressure of 8.5 pounds per square inch gauge (1.62 × $10^5$ pascals). A greenish color in the vapor space indicated thermal decomposition of ethyl chloride.

The bath was then cooled to 105° C. and the reactor was charged with 201 g of commercial heptane solvent (approximately 75% n-heptane, remainder primarily isoheptanes). Additional ethyl chloride was then fed with stirring over a period of about 1.5 hours until a total of 10.2 g (0.158 mole) of ethyl chloride had been added.

The bath was then cooled to 80° C. and 13.2 g (0.143 mole) of gaseous n-butyl chloride was added below the liquid surface with stirring over a period of about 1 hour. The stirring was discontinued and the solids were allowed to settle. Analysis of the solution showed 0.10% chloride by weight and 1.28% magnesium by weight. The latter is equivalent to about 5.82 weight percent n-butylethylmagnesium, which represents a yield of 70% of theory. Hydrolysis of the solution produced a gas containing 48.4 mole percent ethane and 51.6 mole percent n-butane.

EXAMPLES 2–8

Additional preparations were made employing varying ratios of ethyl chloride and n-butyl chloride to test the mutual solubility effect. In each case, the yield of soluble dialkylmagnesium in n-heptane was determined by a magnesium analysis of the solution, and the relative amounts of n-butyl and ethyl groups were determined by analysis of the hydrolysis gas. The results are shown in the following table:

| Alkyl Halide Added | | Hydrolysis Gas Analysis | | % Yield of Soluble $R_2Mg$ |
|---|---|---|---|---|
| n-BuCl (Mole Fraction) | EtCl (Mole Fraction) | n-Butane Mole % | Ethane Mole % | |
| 0 | 1.00 | 0 | 100 | 0 |
| 0.09 | 0.91 | no detectable gas | | 2 |
| 0.24 | 0.76 | 20 | 80 | 35 |
| 0.50 | 0.50 | 52 | 48 | 70 |
| 0.73 | 0.27 | 76 | 24 | 38 |
| 0.89 | 0.11 | 85 | 15 | 5 |
| 1.00 | 0 | 100 | 0 | 0 |

Clearly, the yield of soluble dialkylmagnesium is at a maximum when the n-butyl/ethyl ratio is approximately 1.0.

EXAMPLE 9

This example is offered to demonstrate the preparation of n-butylethylmagnesium using the reverse order of addition of reactants n-butyl and ethyl chlorides. A 10-gallon (0.038 cubic meter) reactor containing an anchor-type agitator and a thermocouple, and heated by an oil jacket, was purged with nitrogen and charged with 18 kilograms of heptane and 1.68 kilograms (0.069 kilogram-mole) of 100-mesh magnesium powder. The reactor was heated to about 95° C. and about 0.2 kilogram of n-butyl chloride was added. After a temperature increase was observed, 1.86 kilograms (0.029 kilogram-mole) of ethyl chloride was fed slowly in order to maintain a pressure within the reactor of 20 pounds per square inch gauge (2.39 × $10^5$ pascals) or less at 100° C.

A temperature increase combined with a drop in reactor pressure observed during the addition indicated ethyl chloride consumption. After completion of the ethyl chloride addition, the reactor temperature was maintained at 100° C. for one hour. n-Butyl chloride was then added slowly to bring the total n-butyl chloride charge to 2.72 kilograms (0.029 Kilogram-mole). Triethylaluminum was added as a viscosity reducing agent. When the solids were settled, the solution was analyzed to show 10.8% n-butylethylmagnesium, which represents a yield of 68.5% of theory. Hydrolysis of the solution produced a gas containing 51.6 mole percent ethane and 48.4 mole percent n-butane.

What is claimed is:

1. A hydrocarbon-soluble compositon of matter comprising di-n-butylmagnesium and diethylmagnesium at a n-butyl:ethyl alkyl group ratio of from about 0.25:1 to about 4:1.

2. A composition according to Claim 1 in which the n-butyl:ethyl alkyl group ratio is from about 0.5:1 to about 2:1.

3. A composition according to Claim 1 in which the n-butyl:ethyl alkyl group ratio is from about 0.8:1 to about 1.25:1.

4. a process for the manufacture of a hydrocarbon solution of a dialkylmagnesium composition comprising
   (e) reacting, in the presence of a hydrocarbon solvent, magnesium metal with a member selected from the group consisting of an ethyl halide in the presence of a magnesium activating agent, and a n-butyl halide,
   (b) either simultaneous to step (a) or subsequent thereto, reacting, in the presence of the solvent of step (a), the unselected member of the group of step (a) with further magnesium metal, to form a mixture of a hydrocarbon solution of a dialkylmagnesium composition and undissolved solids, and
   (c) separating the hydrocarbon solution from the undissolved solids,
all steps being conducted in the substantial absence of both moisture and oxygen.

5. The process of claim 4 in which the hydrocarbon solvent is a member selected from the group consisting of aliphatic, cycloaliphatic, and aromatic hydrocarbons containing 5 to 20 carbon atoms, inclusive.

6. The process of claim 4 in which the hydrocarbon solvent is a member selected from the group consisting of aliphatic, cycloaliphatic and aromatic hydrocarbons containing 6 to 15 carbon atoms, inclusive.

7. The process of claim 4 in which the hydrocarbon solvent is a member selected from the group consisting of aliphatic, cycloaliphatic, and aromatic hydrocarbons which have boiling points between about 69° C. and about 110° C.

8. The process of claim 4 in which the magnesium metal is in the powdered state.

9. The process of claim 4 in which the magnesium metal is comprised of particles of diameter equal to or less than about 150 microns.

10. The process of claim 4 in which the magnesium metal of step (a) is reacted with an ethyl halide in the presence of a magnesium activating agent.

11. The process of claim 10 in which the magnesium of step (a) is thermally activated at a temperature between about 125° C. and about 350° C.

12. The process of claim 4 in which the mole ratio of magnesium to total halides is between about 1.0 and about 2.0.

13. The process of claim 4 in which the mole ratio of magnesium to total halides is between about 1.1 and about 1.3.

14. The process of claim 4 in which the ethyl halide is ethyl chloride and the n-butyl halide is n-butyl chloride.

15. A composition of matter comprising the components
   (a) di-n-butylmagnesium,
   (b) diethylmagnesium, and
   (c) a solvent selected from the group consisting of aliphatic, cycloaliphatic, and aromatic hydrocarbons containing 5 to 20 carbon atoms, inclusive, components (a) and (b) being present in quantities relative to each other such that the n-butyl:ethyl mole ratio is between about 0.25:1 and about 4:1.

16. A composition according to claim 15 in which the solvent is a member selected from the group consisting of aliphatic, cycloaliphatic, and aromatic hydrocarbons containing 6 to 15 carbon atoms, inclusive.

17. A composition according to claim 15 in which the solvent is a member selected from the group consisting of aliphatic, cycloaliphatic, and aromatic hydrocarbons which have boiling points between about 69° C. and about 110° C.

18. A composition according to claim 15 in which the concentration of dialkylmagnesium in the solvent is from about 0.2 weight percent to about 12 weight percent in terms of magnesium.

19. A composition according to claim 15 in which the concentration of dialkylmagnesium in the solvent is from about 1 weight percent to about 5 weight percent in terms of magnesium.

* * * * *

UNITED STATES PATENT AND TRADEMARK OFFICE
CERTIFICATE OF CORRECTION

PATENT NO. : 4,127,507
DATED : November 28, 1978
INVENTOR(S) : Loyd W. Fannin and Dennis B. Malpass It is certified that error appears in the above-identified patent and that said Letters Patent are hereby corrected as shown below:

Column 1, line 11, the word "are" should read --and--.

Column 2, line 31, the word "either" should read --ether--.

Column 6, line 59, the word "in" should read --is--.

Claim 4, line 28, "(e)" should read --(a)--.

Signed and Sealed this

Sixth Day of March 1979

[SEAL]

Attest:

RUTH C. MASON
Attesting Officer

DONALD W. BANNER
Commissioner of Patents and Trademarks